United States Patent
Bor (10) Patent No.: US 12,390,105 B2
(45) Date of Patent: Aug. 19, 2025

(54) EVALUATING AND TREATING EYE FLOATERS

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 379 days.

(21) Appl. No.: 18/049,478

(22) Filed: Oct. 25, 2022

(65) Prior Publication Data

US 2023/0157540 A1 May 25, 2023

Related U.S. Application Data

(60) Provisional application No. 63/281,382, filed on Nov. 19, 2021.

(51) Int. Cl.
*A61B 3/12* (2006.01)
*A61B 3/10* (2006.01)
*G01B 9/02091* (2022.01)

(52) U.S. Cl.
CPC .............. *A61B 3/12* (2013.01); *A61B 3/102* (2013.01); *G01B 9/02091* (2013.01)

(58) Field of Classification Search
CPC . A61B 3/102; A61B 3/12; A61F 9/008; A61F 2009/00874; A61F 2009/00885; G01B 9/02091
See application file for complete search history.

(56) References Cited

U.S. PATENT DOCUMENTS

| | | | |
|---|---|---|---|
| 3,780,979 A | 12/1973 | De | |
| 4,357,088 A | 11/1982 | Pomerantzeff | |
| 5,312,396 A | 5/1994 | Feld | |
| 5,909,270 A | 6/1999 | Moser | |
| 6,142,630 A | 11/2000 | Koester | |
| 6,322,556 B1 | 11/2001 | Gwon | |

(Continued)

FOREIGN PATENT DOCUMENTS

| | | |
|---|---|---|
| AU | 2018274939 B2 | 6/2020 |
| CN | 210009227 U | 2/2020 |

(Continued)

OTHER PUBLICATIONS

Adrian G.H. Podoleanu et al., Combined optical coherence tomograph and scanning laser ophthalmoscope mi nije dostupan besplatno., Electronics Letters, 34 (11), 1998.

(Continued)

*Primary Examiner* — Jack Dinh
(74) *Attorney, Agent, or Firm* — Patterson + Sheridan, LLP (57) ABSTRACT

In certain embodiments, an ophthalmic laser surgical system for treating a floater in an eye comprises a scanning laser ophthalmoscope (SLO) device that: generates an SLO image of a floater shadow cast by the floater onto a retina of the eye, and provides an xy-location of the floater shadow, where the xy-location is related to the xy-scanner. An interferometer device provides a z-location of the floater, where the z-location is relative to the retina. A laser device generates a laser beam and includes a z-focusing component that focuses a focal point of the laser beam onto the z-location of the floater. An xy-scanner directs an SLO beam from the SLO device along an SLO beam path towards the xy-location of the floater shadow, and directs the laser beam from the laser device along the SLO beam path towards the xy-location of the floater shadow.

20 Claims, 8 Drawing Sheets

(56) References Cited

U.S. PATENT DOCUMENTS

| | | |
|---|---|---|
| 6,789,900 B2 | 9/2004 | Van de Velde |
| 7,374,287 B2 | 5/2008 | Van de Velde |
| 7,510,282 B2 | 3/2009 | Ueno |
| 7,520,613 B2 | 4/2009 | Saito et al. |
| 7,703,922 B2 | 4/2010 | Van de Velde |
| 8,480,659 B2 | 7/2013 | Frey et al. |
| 8,652,602 B1 | 2/2014 | Dolla |
| 8,783,868 B2 | 7/2014 | Qiu |
| 8,876,808 B2 | 11/2014 | Feklistov et al. |
| 8,994,753 B2 | 3/2015 | Nakano |
| 9,033,500 B2 | 5/2015 | Utsunomiya |
| 9,603,519 B2 | 3/2017 | Bor et al. |
| 9,675,243 B2 | 6/2017 | Sasak et al. |
| 9,789,002 B2 | 10/2017 | Van De Velde |
| 10,130,511 B2 | 11/2018 | Dantus |
| 10,478,342 B2 | 11/2019 | Dick |
| 10,555,835 B2 | 2/2020 | Schuele et al. |
| 2007/0258094 A1 | 11/2007 | Izatt et al. |
| 2007/0291277 A1 | 12/2007 | Everett |
| 2009/0073384 A1 | 3/2009 | Warden |
| 2009/0137989 A1 | 5/2009 | Kataoka |
| 2009/0196477 A1 | 8/2009 | Cense et al. |
| 2010/0123873 A1 | 5/2010 | Raymond |
| 2010/0152847 A1 | 6/2010 | Padrick |
| 2011/0077557 A1 | 3/2011 | Wing et al. |
| 2012/0281235 A1 | 11/2012 | Murata |
| 2013/0131652 A1 | 5/2013 | Dick |
| 2013/0173029 A1 | 7/2013 | Caldeira et al. |
| 2014/0058367 A1 | 2/2014 | Dantus |
| 2014/0216468 A1 | 8/2014 | Goldshleger |
| 2014/0257257 A1 | 9/2014 | Grant et al. |
| 2014/0268036 A1 | 9/2014 | Ketterling et al. |
| 2014/0276674 A1 | 9/2014 | Lee |
| 2015/0190278 A1 | 7/2015 | Gooding |
| 2015/0342782 A1 | 12/2015 | Mordaunt |
| 2016/0058617 A1 | 3/2016 | Luttrull et al. |
| 2016/0074214 A1 | 3/2016 | Palanker et al. |
| 2016/0074221 A1 | 3/2016 | Tassignon et al. |
| 2016/0166431 A1 | 6/2016 | Vogler et al. |
| 2016/0227999 A1 | 8/2016 | An et al. |
| 2016/0235588 A1 | 8/2016 | Hart et al. |
| 2016/0256324 A1 | 9/2016 | Suzuki |
| 2016/0278629 A1 | 9/2016 | Schuele |
| 2016/0302969 A1 | 10/2016 | Yamamoto |
| 2017/0181625 A1 | 6/2017 | Kawakami et al. |
| 2017/0252213 A1 | 9/2017 | Furuuchi et al. |
| 2017/0326003 A1 | 11/2017 | Schuele et al. |
| 2018/0028354 A1 | 2/2018 | Heeren |
| 2018/0028355 A1 | 2/2018 | Raksi |
| 2018/0140257 A1 | 5/2018 | Govindjee et al. |
| 2018/0206719 A1 | 7/2018 | Adler et al. |
| 2018/0317767 A1 | 11/2018 | Ryan |
| 2018/0353064 A1 | 12/2018 | Soetikno et al. |
| 2018/0368915 A1 | 12/2018 | Xia et al. |
| 2019/0159933 A1 | 5/2019 | Romano et al. |
| 2019/0282403 A1 | 9/2019 | Barrett et al. |
| 2019/0290124 A1 | 9/2019 | Laforest et al. |
| 2019/0313903 A1 | 10/2019 | Mckinnon |
| 2019/0365569 A1 | 12/2019 | Skovgaard et al. |
| 2020/0038241 A1 | 2/2020 | Wang et al. |
| 2020/0060873 A1 | 2/2020 | Heeren |
| 2020/0085292 A1 | 3/2020 | Fukuma et al. |
| 2020/0129336 A1 | 4/2020 | Schuele et al. |
| 2020/0130103 A1 | 4/2020 | Choi |
| 2020/0192080 A1 | 6/2020 | Karam |
| 2020/0196853 A1 | 6/2020 | Van Hemert et al. |
| 2020/0273218 A1 | 8/2020 | Camino et al. |
| 2020/0397289 A1 | 12/2020 | Ralston |
| 2020/0400422 A1 | 12/2020 | Ralston |
| 2021/0100450 A1 | 4/2021 | Amma |
| 2021/0186753 A1 | 6/2021 | Al-Qaisi et al. |
| 2021/0275009 A1 | 9/2021 | Yates |
| 2021/0378507 A1 | 12/2021 | Wallace |
| 2021/0386586 A1 | 12/2021 | Bor |
| 2022/0012459 A1 | 1/2022 | Schwiegerling |
| 2022/0031511 A1 | 2/2022 | Charles |
| 2023/0157889 A1 | 5/2023 | Bor |

FOREIGN PATENT DOCUMENTS

| | | |
|---|---|---|
| CN | 108371542 B | 4/2020 |
| CN | 109196333 B | 12/2020 |
| CN | 111281651 B | 12/2020 |
| CN | 112862782 A | 5/2021 |
| CN | 112587302 B | 6/2021 |
| CN | 112587304 B | 6/2021 |
| DE | 19705044 A1 | 8/1998 |
| DE | 102019007147 A1 | 4/2021 |
| DE | 102019007148 A1 | 4/2021 |
| EP | 0770370 A2 | 2/1997 |
| EP | 1212022 B1 | 3/2005 |
| EP | 1563785 A1 | 8/2005 |
| EP | 1638452 B1 | 10/2006 |
| EP | 1838212 A1 | 10/2007 |
| EP | 2144552 A1 | 1/2010 |
| EP | 1928297 B1 | 11/2010 |
| EP | 2459138 A2 | 6/2012 |
| EP | 2525706 A2 | 11/2012 |
| EP | 2898820 A1 | 7/2015 |
| EP | 3061429 A1 | 8/2016 |
| EP | 2890340 B1 | 2/2017 |
| EP | 3459487 A1 | 3/2019 |
| EP | 3501463 A1 | 6/2019 |
| EP | 3636137 A1 | 4/2020 |
| EP | 3861924 A1 | 8/2021 |
| GB | 2469249 A | 10/2010 |
| JP | 5767014 B2 | 6/2015 |
| JP | 2017176558 A | 10/2017 |
| JP | 6410468 B2 | 10/2018 |
| JP | 2018196821 A | 12/2018 |
| JP | 2018196822 A | 12/2018 |
| JP | 2020022569 A | 2/2020 |
| JP | 6736304 B2 | 7/2020 |
| JP | 6839902 B2 | 2/2021 |
| RU | 2661016 C1 | 7/2018 |
| RU | 2692666 C1 | 6/2019 |
| RU | 2695629 C1 | 7/2019 |
| RU | 2710058 C2 | 12/2019 |
| RU | 2726468 C1 | 7/2020 |
| WO | 9958047 A1 | 11/1999 |
| WO | 0137769 A1 | 5/2001 |
| WO | 0195791 A1 | 12/2001 |
| WO | 2007059189 A2 | 5/2007 |
| WO | 2009033110 A2 | 3/2009 |
| WO | 2009036104 A2 | 3/2009 |
| WO | 2009039315 A2 | 3/2009 |
| WO | 2009059400 A1 | 5/2009 |
| WO | 2010117386 A1 | 10/2010 |
| WO | 2014053824 A1 | 4/2014 |
| WO | 2015131135 A1 | 9/2015 |
| WO | 2015171793 A1 | 11/2015 |
| WO | 2016033590 A1 | 3/2016 |
| WO | 2017062673 A1 | 4/2017 |
| WO | 2017196306 A1 | 11/2017 |
| WO | 2017205857 A1 | 11/2017 |
| WO | 2020074532 A1 | 4/2020 |
| WO | 2020180729 A1 | 9/2020 |
| WO | 2020215359 A1 | 10/2020 |
| WO | 2020216763 A1 | 10/2020 |
| WO | 2020257711 A1 | 12/2020 |
| WO | 2021023799 A1 | 2/2021 |
| WO | 2021049243 A1 | 3/2021 |
| WO | 2021066047 A1 | 4/2021 |
| WO | 2021092211 A1 | 5/2021 |
| WO | 2021183637 A1 | 9/2021 |
| WO | 2022149028 A1 | 7/2022 |
| WO | 2023089416 A1 | 5/2023 |

(56) References Cited

FOREIGN PATENT DOCUMENTS

| WO | 2023089459 A1 | 5/2023 |
|---|---|---|
| WO | 2023097391 A1 | 6/2023 |

OTHER PUBLICATIONS

Chi-Hung Lee, et al., Imaging vitreous floaters and cataracts with optical simulations, Optik, 194, 1-9, 2019.
Christy K. Sheehy et al., High-speed, image-based eye tracking with a scanning laser ophthalmoscope, Biomedical Optics Express, vol. 3, No. 10, 2012.
D. H. Kelly, "Retinal Inhomogeneity. II. Spatial Summation," J. Opt. Soc. Am., pp. 114-119, vol. 1, No. 1 (Jan. 1984).
D. H. Kelly, "Retinal Inhomogeneity. III. Circular-Retina Theory," D.H. Kelly, J. Opt. Soc. Am., pp. 810-819, vol. 2, No. 6 (Jun. 1985).
D.H. Kelly, "Visual Processing of Moving Stimuli," J. Opt. Soc. Am., pp. 216-225, vol. 2, No. 2 (Feb. 1985).
D.H. Kelly,, "Motion and Vision. II. Stabilized Spatio-Temporal Threshold Surface," J. Opt. Soc. Am., pp. 1340-1349, vol. 69, No. 10 (Oct. 1979).
D.H.Kelly, "Retinal Inhomogeneity. I. Spatiotemporal Contrast Sensitivity," J. Opt. Sec. Am., pp. 107-113, vol. 1, No. 1 (Jan. 1984).
Mojana F. et al.. Observations by spectral-domain optical coherence tomography combined with simultaneous scanning laser ophthalmoscopy: imaging of the vitreous, American Journal of Ophthalmol. Apr. 2010; 149(4):641-650.
Nidek, Scanning Laser Ophthalmoscope Mirante SLO/OCT Mirante SLO, https://www.nidek-intl.com/product/ophthaloptom/diagnostic/dia_retina/mirante.htm.
Peter G. J. Barten, "Contrast Sensitivity of the Human Eye and its Effects on Image Quality," Chapter 3, pp. 27-40, Model for the spatial contrast sensitivity of the eye, (1999).
Pointer, J. S., & Hess, R. F. "The contrast sensitivity gradient across the human visual field: With emphasis on the low spatial frequency range,", R. F. Vision Research, 29(9), 1133-1151 (1989).
Sebag J et al., Vitreous and Vitreoretinal Interface, Ch. 21, 2015.
Sebag J., Vitreous and Vision Degrading Myodesopsia. Progress in Retinal and Eye Research Nov. 2020;79.
T Ivanova et al, Vitrectomy for primary symptomatic vitreous opacities: an evidence-based review, Eye (Lond) May 2016;30(5):645-55.
Teri T Kleinberg et al., Vitreous substitutes: a comprehensive review, Survey of Ophthalmology, 56 (4), 2011.
Damodaran et al., "Digital micromirror device based ophthalmoscope with concentric circle scanning", 2017, pp. 2766-2780, vol. 8, No. 5, Biomedical Optics Express.
Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.
Ginner et al., "Wide-Field OCT Angiography at 400 KHz Utilizing Spectral Splitting", Photonics, Oct. 23, 2014, pp. 369-379, vol. 1, No. 4.
Heidelberg Engineering Gmbh, "Spectralis. Hardware Operating Instructions," Version 001, Aug. 2007.
Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.
Hofer et al., "Dispersion encoded full range frequency domain optical coherence tomography", Jan. 5, 2009, pp. 7-24, vol. 17, No. 1, Optics Express, US.
Hofer et al., "Fast dispersion encoded full range optical coherence tomography for retinal imaging at 800 nm and 1060 nm", Mar. 1, 2010, pp. 4898-4919, vol. 18, No. 5, Optics Express.
Leitgeb et al., "Complex ambiguity-free Fourier domain optical coherence tomography through transverse scanning", 2007, pp. 3453-3455, vol. 32, Optics Letters.

Li et al., "DMD-based three-dimensional chromatic confocal microscopy", 2020, pp. 4349-4356, vol. 59, No. 14, Applied Optics.
Martial et al., "Programmable Illumination and High-Speed, Multi-Wavelength, Confocal Microscopy Using a Digital Micromirror", Aug. 2012, e43942, vol. 7, No. 8, PLOS One.
Reznicek Lukas et al., "Wide-Field Megahertz OCT Imaging of Patients with Diabetic Retinopathy", Journal of Diabetes Research, 2015, 5 pages.
Ruggeri et al., "Imaging and full-length biometry of the eye during accommodation using spectral domain OCT with an optical switch", Jul. 1, 2012, pp. 1506-1520, vol. 3, No. 7, Biomedical Optics Express.
Sarunic et al., "Instantaneous complex conjugate resolved spectral domain and swept-source OCT using 3x3 fiber couplers", Feb. 2005, pp. 957-967, vol. 13, No. 3, Optics Express.
Shields et al., "Wide-angle Imaging of the Ocular Fundus", Review of the Ophthalmology, Feb. 15, 2003.
Singh, "Lasers Take Aim At Floaters", Ophthalmology Management, Jul. 1, 2019, pp. 38, 40-42, 59, vol. 23.
Singh, "Modern vitreolysis—YAG laser treatment now a real solution for the treatment of symptomatic floaters", Survey of Ophthalmology, Mar. 3, 2020, pp. 581-591, vol. 65, No. 5.
SunLED, NanoPoint-0201 Series LEDs, published Feb. 15, 2016, www.SunLEDusa.com.
Volk Optical, "Volk Idrees Mid-Vitreous Lens", Dec. 20, 2020, accessed on Dec. 20, 2020 from https://www.volk.com/...s?pr_prod_strat=collection_fallback&pr_rec_pid=4513049018402&or_ref_pid=4513048952866&pr_seq=uniform.
Volk Optical, "Vol Singh Mid-Vitreous Lens", Dec. 20, 2020, accessed on Dec. 20, 2020 from https://www.volk.com/products/singh-mid-vitreous-slit-lamp-lens?_pos+3&_sid=b50c0674f&_ss=r.
Wang et al., "In vivo full range complex Fourier domain optical coherence tomography", Jan. 30, 2007, 054103, vol. 90, Applied Physics Letters.
Wojtkowski et al., "Full range complex spectral optical coherence tomography technique in eye imaging", 2002, pp. 1415-1417, vol. 27, No. 16, Optics Letters.
Yasuno et al., "Simultaneous B-M-mode scanning method for real-time full-range Fourier domain optical coherence tomography", 2006, pp. 1861-1865, vol. 45, No. 8, Applied Optics.
Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.
Zhou et al., "Dual channel dual focus optical coherence tomography for imaging accommodation of the eye", May 25, 2009, pp. 8947-8955, vol. 17, No. 11, Optics Express.
Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.
Chirag P. Shah, et al., YAG Laser Vitreolysis vs Sham YAG Vitreolysis for Symptomatic Vitreous Floaters a Randomized Clinical Trial, JAMA Ophthalmology, Sep. 2017, 918-923, 135-9.
ELLEX Website, Treatment Guidelines—Laser Floater Removal; 2016, Ellex Medical Pty Ltd. E&OE. VB0002E, downloaded Apr. 20, 2017.
Felix Sauvage et al: "Photoablation of Human Vitreous Opacities by Light-Induced Vapor Nanobubbles", ACS Nano, vol. 13, No. 7, Jul. 9, 2019, pp. 8401-8416.
Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.
Michael J. Escuti, et al., "Geometric-Phase Holograms", Optics & Photonics News, pp. 22-29, Feb. 2016.
Milston Rebecca et al: "Vitreous floaters: Etiology, diagnostics, and management", Survey of Ophthalmology, vol. 61, No. 2, Mar. 1, 2016, pp. 211-227.
Nicusor Iftimia et al: "Hybrid retinal imaginer using line-scanning laser ophthalmoscopy and spectral domain optical coherence tomography", Optics Express, vol. 14, No. 26, Dec. 22, 2006.

(56) References Cited

OTHER PUBLICATIONS

Reece Bergstrom, et al., Vitreous Floaters, National Center for Biotechnology Information, May 21, 2020, 4 pages, Bookshelf ID NBK470420, StatPearls Publishing LLC, online.
Wikipedia Encyclopedia, Floater, Wikipedia Encyclopedia, Mar. 29, 2021, online: https://en.wikipedia.org/wiki/rloater?wprov=sfti 1.
Zhang Yunbo et al: "Parallel large-range scanning confocal microscope based on a digital micromirror device", Optik vol. 124, No. 13 (2013), Aug. 4, 2012, pp. 1585-1588.

EVALUATING AND TREATING EYE FLOATERS

TECHNICAL FIELD

The present disclosure relates generally to ophthalmic laser surgical systems, and more particularly to evaluating and treating eye floaters.

BACKGROUND

In ophthalmic laser surgery, a surgeon may direct a laser beam into the eye to treat the eye. For example, in laser vitreolysis, a laser beam is directed into the vitreous to treat eye floaters. Eye floaters are clumps of collagen proteins that form in the vitreous. These clumps can disturb vision with moving shadows and distortions. The laser beam fragments the floaters to improve vision.

BRIEF SUMMARY

In certain embodiments, an ophthalmic laser surgical system for treating a floater in an eye comprises a scanning laser ophthalmoscope (SLO) device, an interferometer device, a laser device, and an xy-scanner. The SLO device generates an SLO image of a floater shadow cast by the floater onto a retina of the eye, and provides an xy-location of the floater shadow, where the xy-location is related to the xy-scanner. The interferometer device provides a z-location of the floater, where the z-location is relative to the retina. The laser device generates a laser beam and includes a z-focusing component that focuses a focal point of the laser beam onto the z-location of the floater. The xy-scanner: receives an SLO beam from the SLO device and directs the SLO beam along an SLO beam path towards the xy-location of the floater shadow; and receives the laser beam from the laser device and directs the laser beam along the SLO beam path towards the xy-location of the floater shadow.

Embodiments may include none, one, some, or all of the following features:

The interferometer device comprises an optical coherence tomography (OCT) device.
The interferometer device comprises a swept source A-scan interferometer (SSASI) device.
The interferometer device comprises multiple reference arms, where each arm corresponds to a z-range of multiple z-ranges within the vitreous, where a z-range is relative to the retina.
The ophthalmic laser surgical system includes an xy-encoder that: detects an angular position of the xy-scanner, where the angular position corresponds to an xy-location expressed in encoder units; and reports the xy-location expressed in encoder units.
The laser device includes adaptive optics that minimize a spot size of the laser beam.
The laser device includes adaptive optics that maximize a feedback signal to optimize the laser beam.
The laser device includes an optical element that form the laser beam as a Bessel or Bessel-like long focal length beam.
The computer: performs image processing on the SLO image of the floater shadow cast onto the retina; evaluates the floater shadow to determine if the floater can cause a visual disturbance; and outputs results of the evaluation. The computer may determine if the floater shadow is cast onto a foveal region or a parafoveal region of the eye. The computer may determine if the floater shadow is larger than a critical shadow size. The computer may generate and output a report comprising the SLO image of the floater shadow cast onto the retina and educational information about the floater or a recommended treatment for the floater.

In certain embodiments, a method for treating a floater in an eye comprises generating, by a scanning laser ophthalmoscope (SLO) device, an SLO image of the floater shadow cast by the floater onto the retina of the eye. The xy-location of the floater shadow, where the xy-location is related to an xy-scanner, is provided by the SLO device. The z-location of the floater, where the z-location is relative to the retina, is provided by an interferometer device. A laser beam is generated by a laser device. The focal point of the laser beam is focused onto the z-location of the floater by a z-focusing component of the laser device. An SLO beam is received by the xy-scanner from the SLO device and directed along an SLO beam path towards the xy-location of the floater shadow. The laser beam is received by the xy-scanner from the laser device and directed along the SLO beam path towards the xy-location of the floater shadow.

Embodiments may include none, one, some, or all of the following features:

The interferometer device comprises an optical coherence tomography (OCT) device.
The interferometer device comprises a swept source A-scan interferometer (SSASI) device.
The angular position of the xy-scanner, where the angular position corresponds to an xy-location expressed in encoder units, is detected by an xy-encoder. The xy-location expressed in encoder units is reported by the xy-encoder.
Image processing of the SLO image of the floater shadow cast onto the retina is performed by the computer. The floater shadow is evaluated to determine if the floater can cause a visual disturbance. Results of the evaluation are output by the computer. The floater shadow may be evaluated by determining if the floater shadow is cast onto a foveal region or a parafoveal region of the eye or by determining if the floater shadow is larger than a critical shadow size.
A report is generated by the computer. The report includes the SLO image of the floater shadow cast onto the retina, and educational information about the floater or a recommended treatment for the floater.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In laser vitreolysis surgery, a laser beam should be accurately and precisely directed at a floater in order to treat the floater safely and effectively. However, floaters are extremely difficult to visualize with known laser vitreolysis systems. Light reflected from the floaters and background typically does not yield images with enough contrast to clearly distinguish the floaters from the background. Thus, accurately determining the location of the floater is challenging. Moreover, known laser vitreolysis systems cannot provide satisfactory image guidance for the laser beam. In these systems, the imaging beam for generating images and the laser beam for treating the floater are often not aligned, resulting in inaccurate laser beam guidance.

Certain embodiments of ophthalmic laser surgical systems described herein address these problems. For example, a scanning laser ophthalmoscope (SLO) device generates an image of the retina that shows the floater shadow cast by a floater onto the retina. The floater shadow yields an image with a higher contrast, and thus can be used to gather accurate information about the size, density, location, and clinical significance of the floater.

As another example, the SLO device provides xy-locations in encoder units of an xy-scanner. The encoder units represent the angular orientation of the mirrors of the xy-scanner. Providing locations in encoder units is easier than converting encoder information into linear distances (e.g., millimeter distances) on the retina because the SLO beam propagates through several curved optical surfaces (e.g., surfaces of the cornea, natural lens, and/or intraocular lens).

As yet another example, embodiments include an interferometer device (e.g., a swept source full depth optical coherence tomography (SSFD OCT) devices or a swept source A-scan interferometer (SSASI) device) that provides the z-location of the floater relative to the retina. As yet another example, the treatment laser beam shares an xy-scanner with the SLO and interferometric beams, allowing the laser beam to co-propagate with the SLO and interferometric beams. Since the SLO, interferometric, and laser devices use the same xy-scanner, the floater can be treated with high spatial accuracy.

Figure 1:
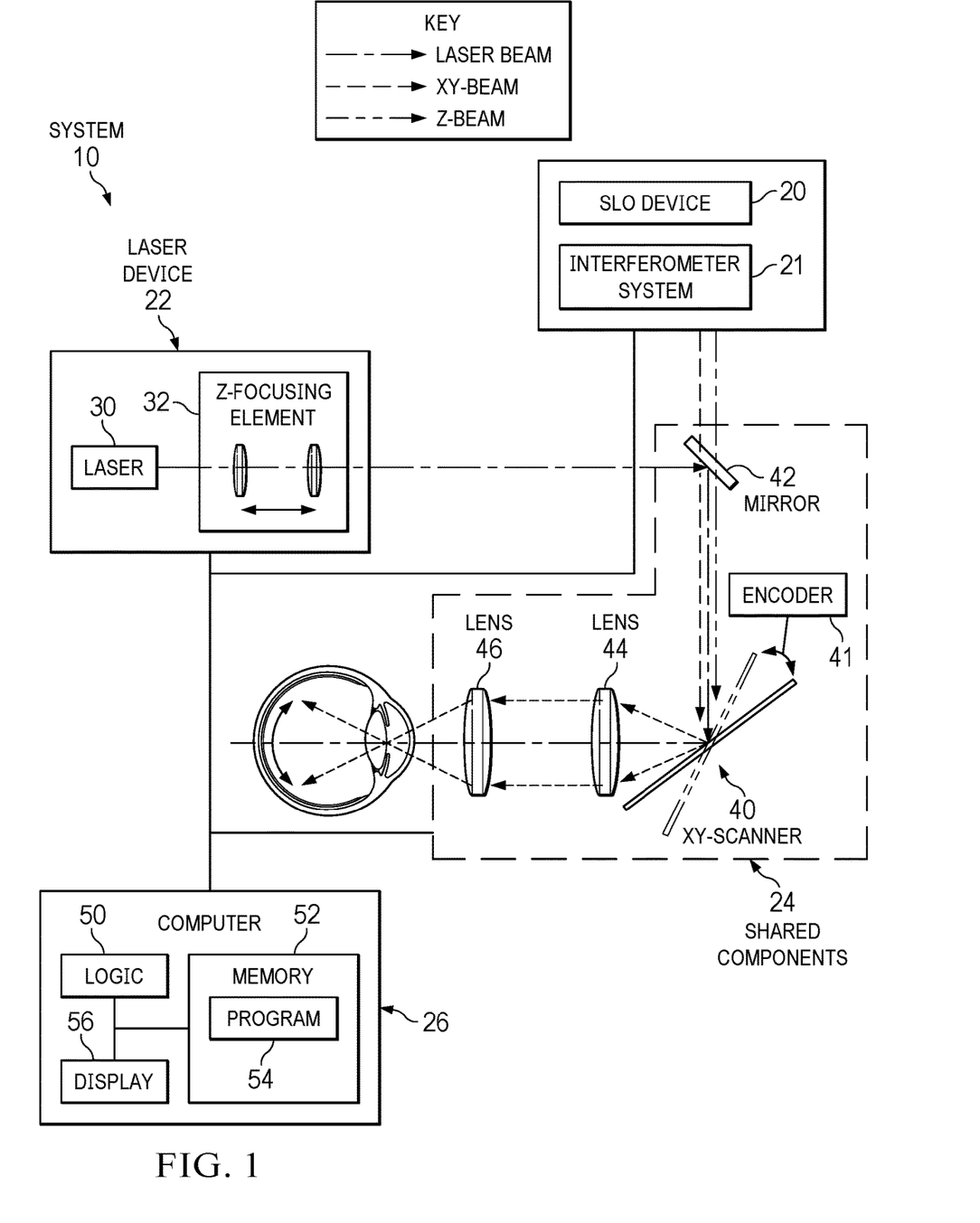
FIG. 1 illustrates an example of an ophthalmic laser surgical system that may be used to treat a floater in an eye, according to certain embodiments.

FIG. 1 illustrates an example of an ophthalmic laser surgical system 10 that may be used to treat a floater in an eye, according to certain embodiments. As an overview, system 10 includes a scanning laser ophthalmoscope (SLO) device 20, an interferometer device 21, a laser device 22, one or more shared components 24, and a computer 26, coupled as shown. Laser device 22 includes an ultrashort pulse laser 30 and a z-focusing component 32, coupled as shown. Shared components 24 include an xy-scanner 40, an xy-encoder 41, and optical elements (such as a mirror 42 and lenses 44 and 46), coupled as shown. Computer 26 includes logic 50, a memory 52 (which stores a computer program 54), and a display 56, coupled as shown.

As an overview of operation of system 10, SLO device 20 generates an SLO image of the floater shadow cast by a floater onto the retina. SLO device 20 also provides the xy-location of the floater shadow, where the xy-location is related to xy-scanner 40. Interferometer device 21 provides the z-distance of the floater from the retina (which may be referred to as the z-location). Z-focusing component 32 of laser device 22 receives the z-location of the floater from interferometer device 21 and is designed to focus the focal point of the laser beam onto the z-location of the floater. Xy-scanner 40 receives an SLO beam from the SLO device and in response to a command from computer 26 can direct the SLO beam along an SLO beam path towards the xy-location of the floater shadow. Xy-scanner 40 also receives the laser beam from the laser device and directs the laser beam along the SLO beam path towards the xy-location of the floater shadow.

As an example of aiming the laser beam, an image of the eye includes a reticle, which is a graphical overlay (e.g., crosshairs) that indicates where the beam is currently aimed in the xy-plane. The user or computer 26 places the reticle over the floater shadow in the image to aim the beam at the floater. Xy-encoder 41 detects the position of xy-scanner 40 to determine the xy-location of the reticle (in encoder units) centered at the floater shadow.

Turning to the parts of the system, SLO device 20 utilizes confocal laser scanning to generate images of the interior of the eye. In certain embodiments, SLO device 20 generates an image of the floater shadow that a floater casts on the retina and provides the xy-location of the floater shadow in encoder units. An example of SLO device 20 is described in more detail with reference to FIG. 3.

Interferometer device 21 provides the z-location of the floater relative to the retina. Interferometer device 21 has any suitable interferometer, e.g., a Fourier domain type (such as a swept source or a spectral domain type) that utilizes a fast Fourier transform (FFT). Examples of interferometer device 21 include an optical coherence tomography (OCT) device (such as a swept-source OCT device) and a swept source A-scan interferometer (SSASI) device (where a SASSI device performs only A-scans). Swept Source OCT and SSASI devices have a measuring range up to about 30 millimeters (mm) that can measure the depth (i.e., z-location relative to the retina) within the full length of the eye from the cornea to the retina. An example of an interferometer device 21 with multiple reference arms is described in more detail with reference to FIG. 5.

As an example of operation of interferometer device 21, a splitter splits the light into measurement light and reference light. The reference light is directed to a reference arm system. The measurement light is directed through shared components 24 towards the eye and is reflected by surfaces and/or objects within the eye (e.g., the anterior and posterior surfaces of the cornea and natural or intraocular lens, the retina, and floaters). An interferometer combines the reflected measurement and reference light, which creates interference that in turn causes spectral modulation of the intensity. The frequency of the modulation is used to determine the depth at which the light was reflected, and the amplitude of the modulation carries information about the intensity of the back-reflected beam. The calculations may involve, e.g., Fourier analysis.

A measurement made along one direction of the xy-scanner is an A-scan. An example of an A-scan is described in more detail with reference to FIG. 4A. Multiple A-scans made with the movement of a scanner mirror of the xy-scanner is a B-scan. A B-scan may be used to visualize a side view of a slice of the eye. An example of a B-scan is described in more detail with reference to FIG. 4B. Multiple B-scans may be used to generate a 3D image of the eye.

The OCT images may be used to identify the location of the surfaces (e.g., the anterior and/or posterior surfaces) of a floater, the lens (natural or intraocular lens (IOL)), and/or the retina. Accordingly, the OCT images can indicate the z-location and thickness of the floater in the z-direction.

Turning to laser device 22, ultrashort pulse laser 30 generates a laser beam with any suitable wavelength, e.g., in a range from 400 nm to 2000 nm. Laser device 22 delivers laser pulses at any suitable repetition rate (e.g., a single pulse to 200 megahertz (MHz)). A laser pulse has any suitable pulse duration (e.g., 20 femtoseconds (fs) to 1000 nanoseconds (ns)), any suitable pulse energy (e.g., 1 nanojoule (nJ) to 10 millijoule (mJ)), and a focal point of any suitable size (e.g., 1 to 30 microns (μm)). In a particular embodiment, the laser is a picosecond or femtosecond laser with a repetition rate that exceeds 100 pulses per second (pps).

In certain embodiments, laser device 22 or the optical delivery system includes adaptive optics. The adaptive optics correct phase front errors of the laser beam to minimize the spot size of the laser beam, which in turn minimizes the required pulse energy (e.g., a few microjoules (uJ) to the nanojoule (nJ) range) and radiation exposure at the retina. In certain embodiments, adaptive optics are used to optimize the laser beam prior to treatment. In the embodiments, the laser beam is directed near the floater using subthreshold energy levels. A feedback signal (e.g., a two-photon fluorescence or a second harmonic feedback signal) from the vitreous is detected. Adaptive optics (e.g., an adaptive mirror) in the laser beam path are used to maximize the intensity of the feedback signal to minimize aberrations of the eye and the optical system.

In certain embodiments, laser device 22 includes an optical element that forms a Bessel or Bessel-like long focal length beam, which may increase the efficiency of floater destruction. In general, as compared with Gaussian beams, Bessel beams have a 1.6× smaller spot size, longer focal length (resulting in shorter treatment time), and larger divergence (yielding a larger spot size on the retina, reducing risk of retinal damage). Examples of optical elements that form Bessel or Bessel-like long focal length beams include an axicon, circular grating, proper phase plate, spatial light modulator (SLM), and Fabry-Perot interferometer.

Z-focusing component 32 longitudinally directs the focal point of the laser beam to a specific location in the direction of the floater shadow. In certain embodiments, z-focusing component 32 receives the z-location of the floater from interferometer device 21 (and may receive it via computer 26), and directs the laser beam towards the z-location of the floater. Z-focusing component 32 may include a lens of variable refractive power, a mechanically tunable lens, an electrically tunable lens (e.g., Optotune lens), an electrically or mechanically tunable telescope. In certain embodiments, laser device 22 or the optical delivery system also includes a fast xy-scanner used in tandem with z-focusing component 32 to, e.g., create a 3D focal spot pattern. Examples of such scanners include galvo, MEMS, resonant, or acousto-optical scanners.

Shared components 24 direct beams from SLO device 20, interferometer device 21, and laser device 22, respectively, towards the eye. Because SLO, interferometer, and/or laser beams share components 24, the beams are affected by the same optical distortions (e.g., fan distortion of scanners, barrel or pillow distortions of the scanner lens, refractive distortions from the inner eye surfaces, and other distortions). The distortions affect the beams in the same way, so the beams propagate along the same path. This allows for aiming the laser beam precisely at the floater.

As an overview of operation of shared components 24, mirror 42 directs a beam (SLO, interferometer, and/or laser beam) towards xy-scanner 40, which transversely directs the beam towards lens 44. Lenses 44 and 46 direct the beam towards eye. Shared components 24 may also provide spectral and polarization coupling and decoupling of SLO, interferometer, and laser beams to allow the beams to share the same path.

Turning to the details of shared components 24, in certain embodiments, xy-scanner 40 receives the xy-location of the floater shadow from SLO device 20, and directs the SLO, interferometer, and/or laser beam towards the xy-location. Xy-scanner 40 may be any suitable xy-scanner that transversely directs the focal point of the beam in the x- and y-directions and changes the angle of incidence of the beam into the pupil. For example, xy-scanner 40 includes a pair of galvanometrically-actuated scanner mirrors that can be tilted about mutually perpendicular axes. As another example, xy-scanner 40 includes an acousto-optical crystal that can acousto-optically steer the beam. As another example, xy-scanner 40 includes a fast scanner (e.g., a galvo, resonant, or acousto optical scanner) that can create, e.g., a 2D matrix of laser spots.

Xy-encoder 41 detects the angular position of xy-scanner 40 and reports the position as the xy-location measured in angular units. For example, xy-encoder 41 detects the angular orientations of the galvanometer mirrors of xy-scanner 40 in encoder units. Xy-encoder 41 may report the position in encoder units to SLO device 20, interferometer device 21, laser device 22, and/or computer 26. Since SLO device 20, interferometer device 21, and laser device 22 share xy-scanner 40, computer 26 can use the encoder units to instruct system 20 and device 22 where to aim their beams, making it unnecessary to perform the computer-intensive conversion from encoder units to a length unit such as millimeters. Xy-encoder 41 reports the positions at any suitable rate, e.g., once every 5 to 50 milliseconds (ms), such as every 10 to 30 or approximately every 20 ms.

Shared components 24 also include optical elements. In general, an optical element can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical elements include mirror 42 and lenses 44 and 46. Mirror 42 may be a trichroic mirror. Lenses 44 and 46 may be scanning optics of an SLO device.

Computer 26 controls components of system 10 (e.g., SLO device 20, interferometer device 21, laser device 24, and/or shared components 24) in accordance with a computer program 54. Computer 26 may be separated from components or may be distributed among system 10 in any suitable manner, e.g., within SLO device 20, interferometer device 21, laser device 24, and/or shared components 24. In certain embodiments, portions of computer 26 that control SLO device 20, interferometer device 21, laser device 24, and/or shared components 24 may be part of SLO device 20, interferometer device 21, laser device 24, and/or shared components 24, respectively.

Computer 26 controls the components of system 10 in accordance with a computer program 54. Examples of computer programs 54 include floater shadow imaging, floater shadow tracking, image processing, floater evaluation, retinal exposure calculation, patient education, and insurance authorization programs. For example, computer 26 uses a computer program 54 to instruct SLO device 20, interferometer device 21, laser device 24, and/or shared components 24 to image a floater shadow and focus a laser beam at the floater.

In certain embodiments, computer 26 uses an image processing program 54 to analyze the digital information of the image to extract information from the image. In certain embodiments, image processing program 54 analyzes an image of a floater shadow to obtain information about the floater. For example, program 54 detects a floater by detecting a darker shape in an image (using, e.g., edge detection or pixel analysis) that may be the floater shadow. As another example, program 54 detects the shape and size of a floater shadow, which indicate the size and shape of the floater. As another example, program 54 detects the tone or luminance of the floater shadow, which indicates the density of the floater. In certain embodiments, computer 26 uses a tracking program 54 to track a floater shadow, as described in more detail with reference to FIG. 6.

In certain embodiments, computer 26 determines the radiant exposure at the retina from a laser pulse directed at a particular z-location. The determination may consider any suitable factors, e.g., laser pulse energy, laser radiation wavelength, number of laser pulses, laser pulse duration, cone angle of the focused laser beam, and the focus to the retina. For example, the exposure can be calculated using the laser spot size of the laser beam and the distance between the floater and retina. The radiant exposure should be less than a maximum radiant exposure, which may be determined in accordance with accepted standards. For example, the maximum radiant exposure may be set in accordance with ANSI Z80.36-2016. If the radiant exposure exceeds the maximum radiant exposure of the retina, lens, and/or IOL, computer 26 may modify any suitable factor (e.g., lower the pulse energy), provide a notification to the user, and/or prevent firing of the laser beam as an important safety feature.

System 10 may be used as a diagnostic tool and/or a treatment device, which can save space in an ophthalmic office. In certain embodiments, system 10 can be used as a diagnostic tool. In the embodiments, the laser is not activated, and system 10 can display images of the floater shadows, which can help many people over the age of 50 who have vitreous floaters. In most cases, floaters do not affect the visual acuity or visual performance of the patients. However, moving floaters attract the visual attention of the patients, annoying them. Showing images of floater shadows moving on the fovea to patients and explaining that floaters do not cause blindness and the visual effects are similar to that in movie theaters may calm down many patients. The patients may decide to not to treat the floaters, but accept them as an age-related benign condition.

In the embodiments where system 10 is used as a diagnostic tool, certain computer programs may be appropriate. In certain embodiments, computer 26 uses a floater evaluation and diagnosis program 54 to evaluate a floater to determine if the floater is clinically significant, i.e., affects vision. In certain embodiments, display 56 of computer 26 displays images (such as a video) of a floater shadow so a user can evaluate the floater as described in more detail with reference to FIGS. 2 and 8. In other embodiments, computer 26 uses image processing to evaluate the floater shadow as described in more detail with reference to FIGS. 2 and 8.

In certain embodiments, a patient education program 54 generates a patient education report describing floater shadows found within a patient's eye. The report may include, e.g., images (such as a video) of a floater shadow found within a patent's eye; educational information about vitreous floaters; images of the vitreous pre- and post-treatment show the effectiveness of treatment; and/or other information to be provided to a patient. Computer 26 may output the report in any suitable manner. For example, computer 26 may store the report in memory 52, display the report in display 56, or send the report to, e.g., the user or patient.

In certain embodiments, a health insurance authorization program 54 generates an authorization report to obtain approval to treat floaters found within a patient's eye. The report may include, e.g., images (such as a video) of a floater shadow found within a patent's eye; patient information (e.g., identifying information, medical records); a recommended treatment; and/or other information required to obtain approval for treatment. Computer 26 may output the report in any suitable manner. For example, computer 26 may store the report in memory 52, display the report in display 56, or send the report to, e.g., the user, patient, or insurance company.

Involuntary and voluntary eye movements (e.g., saccadic and microsaccadic movements, drift, and tremor) can make laser treatment difficult. To reduce movement, the eye can be stabilized during treatment in any suitable manner to reduce movement of the eye. For example, the treated eye and/or the other eye can be stabilized using a fixation light. As another example, a patient interface or handheld surgical contact lens can be used to mechanically stabilize the eye. In addition, movement of the treated eye and/or the other eye can be tracked in any suitable manner. Any suitable portion of the eye (e.g., pupil, pupil edge, iris, blood vessels) and/or reflections from the eye (e.g., Purkinje reflections) can be tracked.

Figure 2:
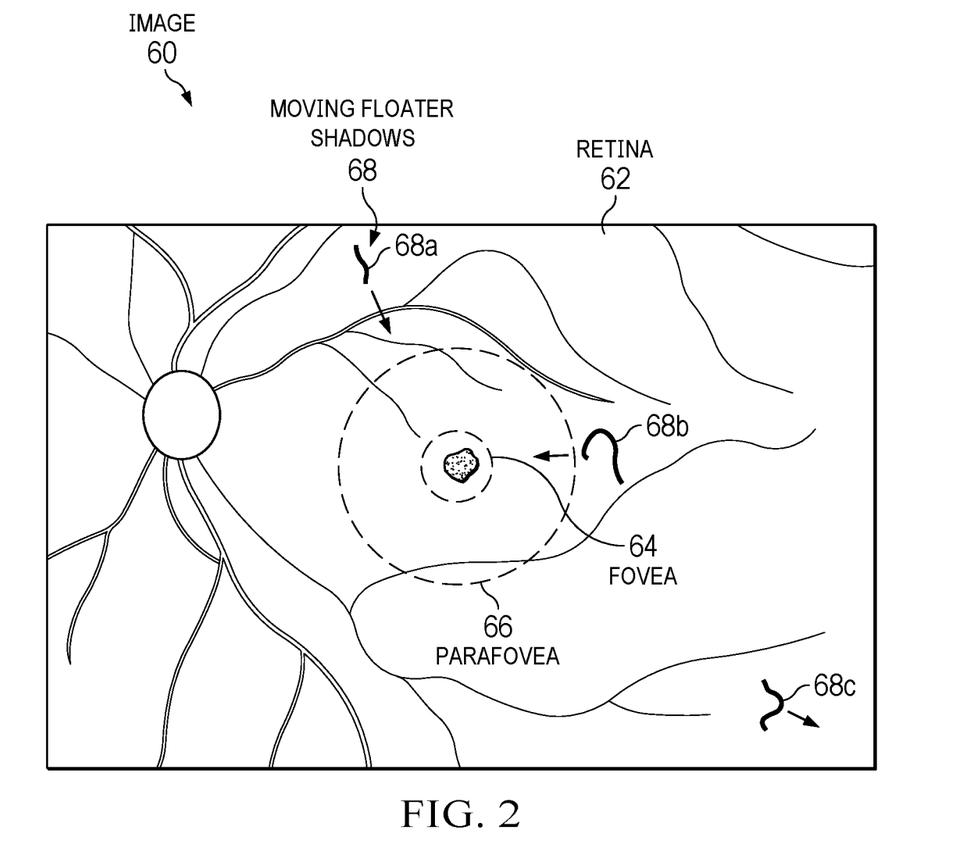
FIG. 2 illustrates an example of a retinal image that may be generated by the system of FIG. 1.

FIG. 2 illustrates an example of a retinal image 60 that may be generated by system 10 of FIG. 1. Image 60 shows the retina 62 of an eye, with a foveal region (or fovea) 64 and a parafoveal region (or parafovea) 66. Generally, fovea 64 has a visual angle of approximately +/− one degree, and parafovea 66 has a visual angle of approximately +/− seven degrees. Image 60 also shows floater shadows 68 (68a, 68b, 68c) that floaters cast on retina 62. In general, non-moving shadows are not caused by floaters, and may be caused by, e.g., corneal or lens opacities or anatomical changes of the retina, so floater treatment is not concerned with non-moving shadows.

A floater may be regarded as clinically significant if it can cause a visual disturbance, which can be determined from any suitable features of the floater shadow, e.g., the size and/or density of the shadow, proximity of the shadow to the fovea and/or parafovea, and/or the track of the shadow relative to the fovea and/or parafovea. As an example, a floater can cause a visual disturbance if it permanently or transiently casts a shadow 68 on fovea 64 or can cause distraction or annoyance if it permanently or transiently casts a shadow 68 on parafovea 66. Accordingly, if a floater shadow falls within or is predicted to move within fovea 64 and/or parafovea 66, the floater may be designated as clinically significant. As another example, floater shadow 68 can be used to estimate the size and density of the floater. Larger, denser floaters are more likely to cause a visual disturbance. Thus, a shadow 68 larger than a critical shadow size can indicate a clinically significant floater. A shadow 68 with a higher contrast relative to the background may indicate a clinically significant floater.

In some cases, a clinically significant floater may not be in a position to be safely treated. For example, floater shadow 68 may be too close to fovea 64, large blood vessels, the optic nerve head, or other sensitive area to be treated. In certain embodiments, computer 26 uses image processing to determine if a floater is in a position to be safely treated, and provides a notification if it is not, as described in more detail with reference to FIG. 1.

In certain embodiments, a user such as a surgeon may determine significance from the displayed images (such as a video) of the floater shadow. An image processing program can assist the user in making the decision. In other embodiments, the computer can use image processing and target evaluation computer programs to determine significance from the image, as described in more detail with reference to FIG. 8.

Figure 3:
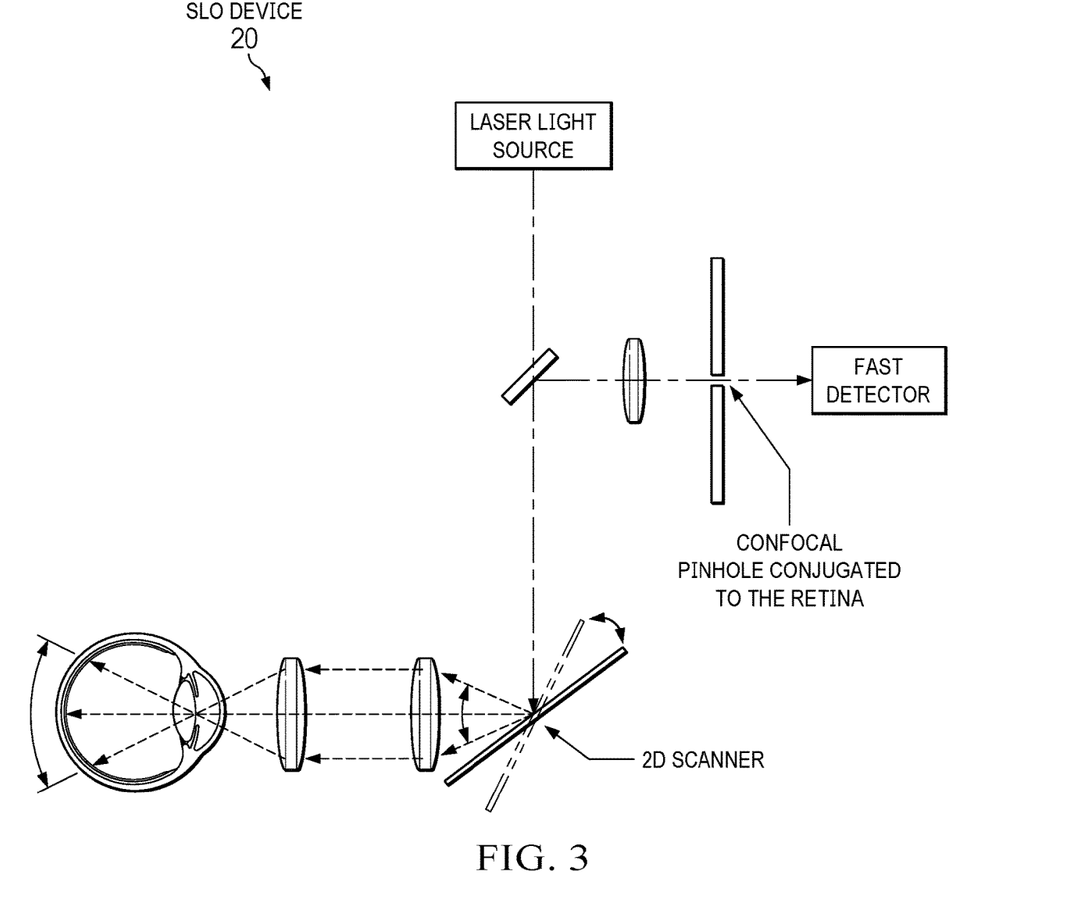
FIG. 3 illustrates an example of an SLO device that may be used in the system of FIG. 1.

FIG. 3 illustrates an example of SLO device 20 that may be used in system 10 of FIG. 1. In an example of operation, laser beam is focused onto the retina and scanned over an angular range (e.g., a 20 to 40 degree angular range) by a 2D xy-scanner (e.g., a galvo scanner). The light reflected from the retina is focused by a lens onto a pinhole. The pinhole is optically conjugated to the retinal surface such that only the light reflected from the retina is detected by a detector (e.g., a sensitive high-speed detector) and the other light is filtered out. The intensity of the back-reflected light is displayed as a 2D enface image, where the x- and y-axes of the image represent readings of an angular encoder of the xy-scanner. The xy-scanner and detector may be sufficiently fast to display the enface image as a video with any suitable frame rate (e.g., up to about 100 frames per second).

The SLO image displays the local intensity of the back-reflected light from the retina, which shows the anatomical features of the retina (e.g., vasculature, optic nerve head, and certain retinal decease). The image also shows shadows cast by floaters. Floaters are opaque objects that attenuate an incident laser beam, causing shadows on the retina. Floaters move with the partially liquified vitreous, so they cause moving shadows. The movement distinguishes floater shadows from static images of, e.g., anatomical objects of the retina or other parts of the eye.

Figure 4A:
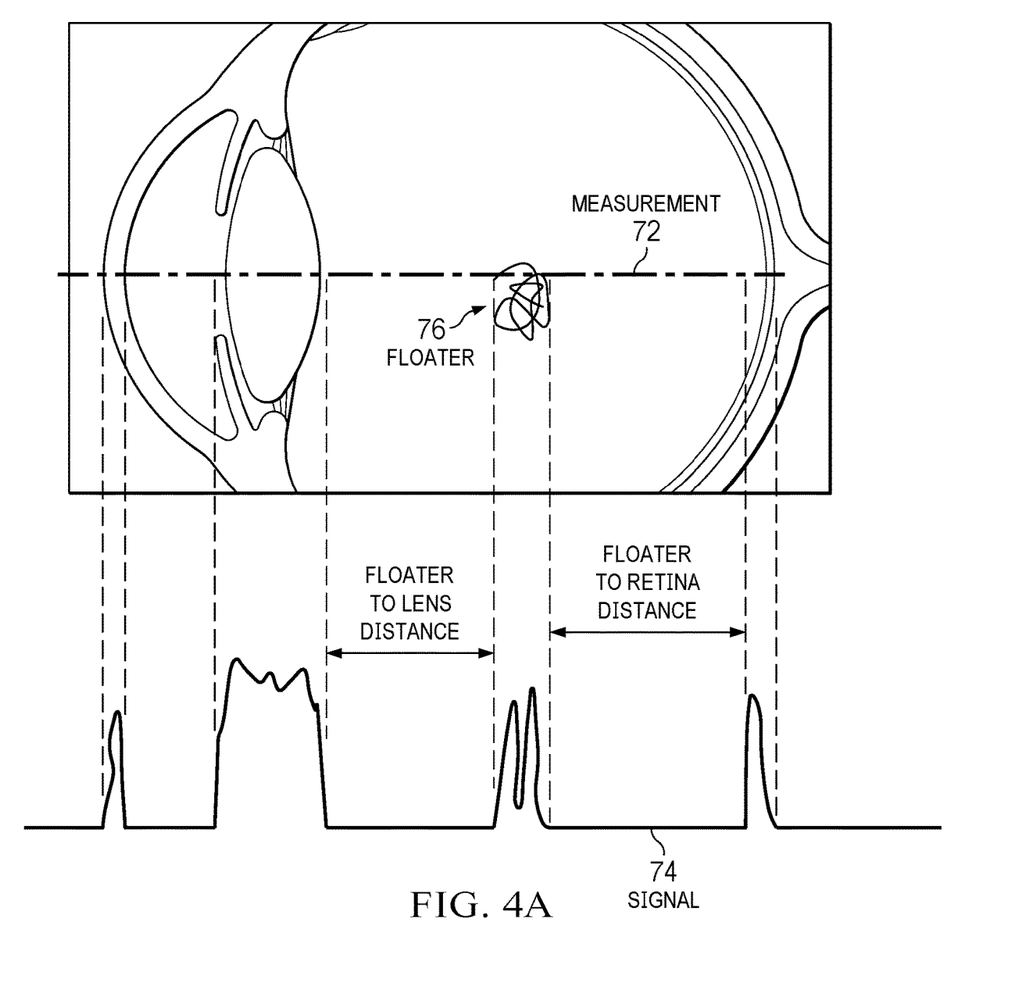
FIG. 4A illustrates examples of a depth measurement that may be performed by an interferometer device.

FIG. 4A illustrates examples of a depth measurement 72 that may be performed by an interferometer device, such as an optical coherence tomography (OCT) device (such as a swept-source OCT device) or a swept source A-scan interferometer (SSASI) device. Depth measurement 72 may comprise an A-scan that extends from the cornea through the lens and floater 76 to the retina. The signal 74 from the A-scan indicates reflections from the cornea, lens, floater, and retina, which can used to determine the z-locations of these features relative to the retina.

Figure 4B:
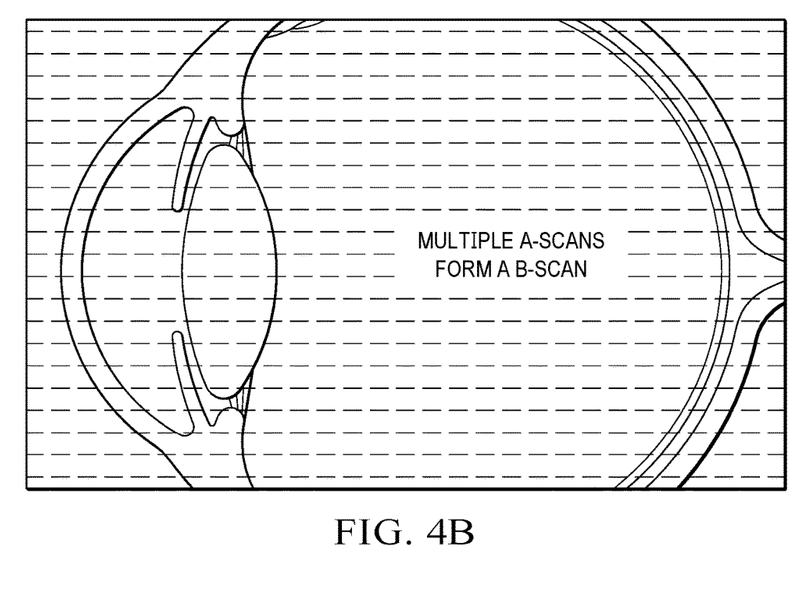
FIG. 4B illustrates an example of multiple A-scans forming a B-scan.

FIG. 4B illustrates an example of multiple A-scans forming a B-scan. Multiple A-scans made with the movement of a scanner mirror of the xy-scanner (or other movement that yields a plane of A-scans) is a B-scan. A B-scan may be used to visualize a side view of a slice of the eye.

Figure 5:
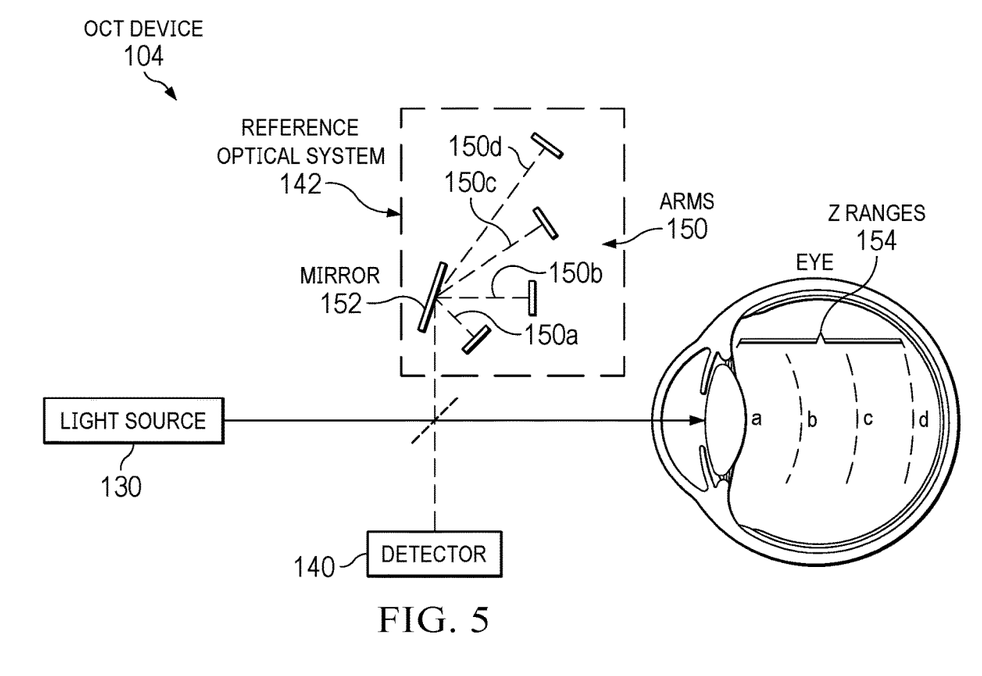
FIG. 5 illustrates an example of interferometer device that may be used in the system of FIG. 1.

FIG. 5 illustrates an example of interferometer device 21 that may be used in system 10 of FIG. 1. Interferometer device 21 may be an optical coherence tomography (OCT) device (such as a swept-source OCT device) or a swept source A-scan interferometer (SSASI) device. In the example, interferometer device 21 includes reference optical system 142 (with arms 150 (150*a* to 150*d*) and mirror 152), light source 130, and detector 140, coupled as shown. Light source 130 provides light for the interferometer beam. Examples of light source 130 include a super-luminescent or swept-source diode, such as a super-luminescent diode. Detector 140 detects the interference signal light. Examples of detector 140 include a high-resolution spectrometer or fast diode.

Reference optical system 142 includes any suitable number of reference arms 150 (150*a* to 150*d*) and galvo mirror 152. Each reference arm 150 is used for a different z-range 154 of the eye. For example, arm 150*a* is used for z-range 154*a*, arm 150*b* is used for z-range 154*b*, arm 150*c* is used for z-range 154*c*, and arm 150*d* is used for z-range 154*d*. In certain embodiments, the z-ranges 154 may overlap slightly, e.g., 1 mm or less. In the example, each z-range 154 corresponds to approximately 6 mm of vitreous, yielding coverage of approximately 24 mm. Galvo mirror 152 is used to direct the beam to the arm 150 for a particular z-range 154, and may switch between arms in, e.g., less than 5 ms, such as approximately one ms. Floaters have limited movement in the z-direction, so once an arm 150 for a z-range is selected, there may be little need to switch to a different arm 150. Computer 26 can join together images from different z-ranges 154 to yield an image of the length of the eye. In certain embodiments, interferometric devices, such as a swept source OCT device or a swept source A-scan interferometer (SSASI) device, may have measurement range as large as 35 mm, so they do not need multiple reference arms.

Figure 6:
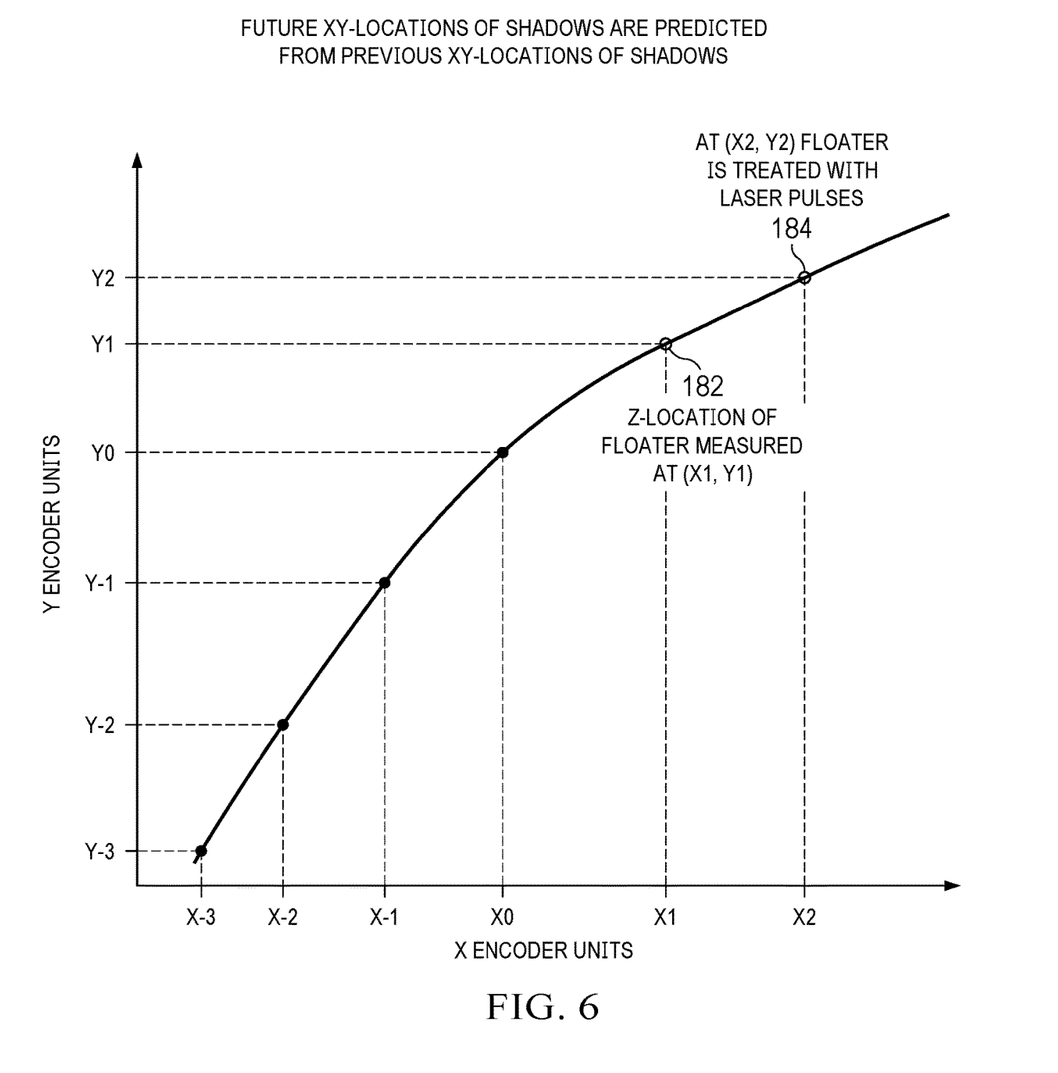
FIG. 6 is a graph illustrating an example of tracking and predicting the xy-location of a floater shadow, which may be performed by the system of FIG. 1, according to certain embodiments.

FIG. 6 is a graph 180 illustrating an example of tracking and predicting the xy-location of a floater shadow, which may be performed by system 10 of FIG. 1, according to certain embodiments. In the embodiments, a computer uses a tracking program to track and/or predict the movement of a floater shadow. For example, the computer performs image analysis of retinal images to track the movement of the floater shadow to track the floater. As discussed with reference to FIG. 2, floater treatment is concerned with moving shadows.

In the example, the xy-location is given in encoder units (which may be provided by encoder 41). Variable t represents time t=−3, −2, −1, 0, 1, 2, where t=0 is the current time, t=−3, −2, −1 is the past time, and t=0, 1, 2 is the future time. Yt represents the y-location in encoder units at time t, and Xt represents the x-location in encoder units at time. The tracking program predicts the future xy-locations by extrapolating from past xy-locations.

In the example, the interferometer device measures the z-location position of the floater at the xy-location (x1, y1) at time t=1, shown at reference number 182. The measurement may be performed a few milliseconds prior to firing the laser. At the xy-location (x2, y2) at time t=2, shown at reference number 184, the laser device fires a laser beam comprising laser pulses. The laser beam is directed by the xy-scanner to the xy-location (x2, y2) and is focused by the z-focusing component at the z-location. In general, floaters do not move much in the z-direction, so the z-location measured at t=1 may be sufficiently close to the z-location at t=2.

Figure 7:
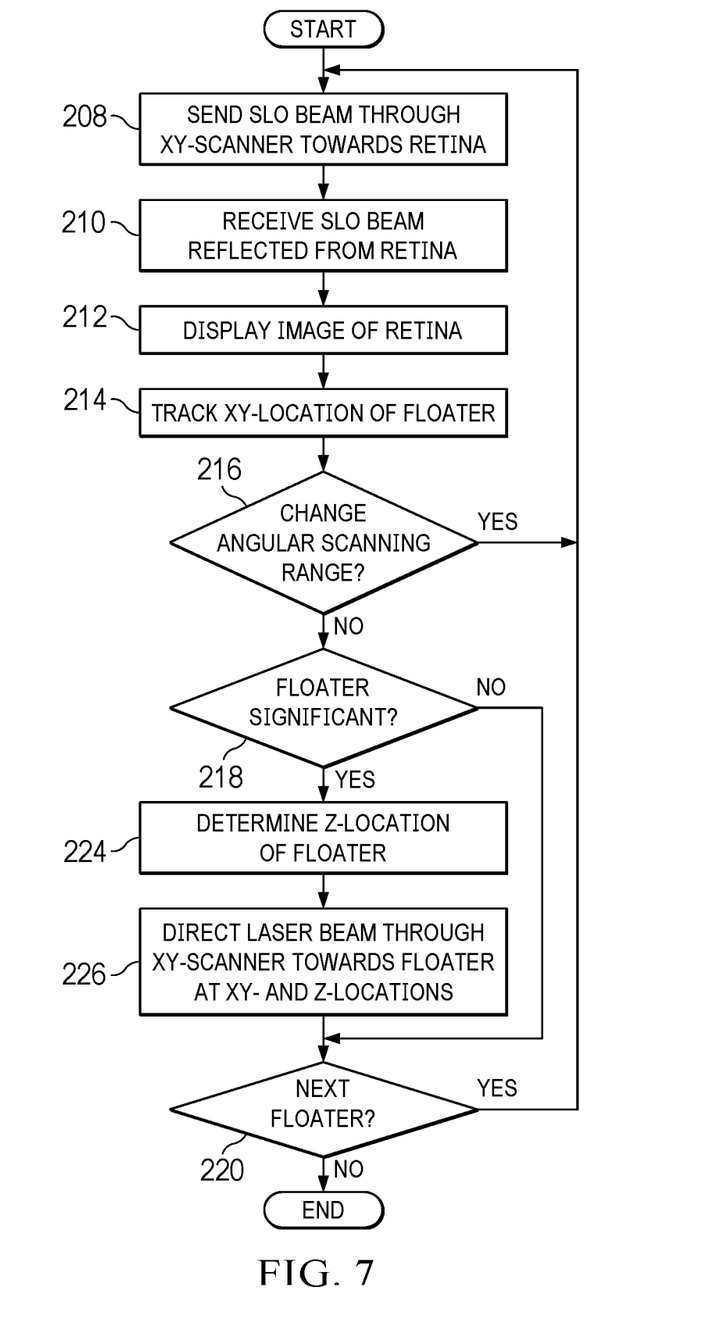
FIG. 7 illustrates an example of a method for treating a floater in an eye, which may be performed by the system of FIG. 1, according to certain embodiments.

FIG. 7 illustrates an example of a method for treating a floater in an eye, which may be performed by system 10 of FIG. 1, according to certain embodiments. The method starts at step 208, where an SLO device sends an SLO beam through an xy-scanner towards the eye. During an initial viewing, the SLO device scans a larger angular range in order to identify a region with a floater shadow. For example, the larger angular range may be 20 to 60 degrees, such as 30 to 50 degrees, e.g., approximately 40 degrees, with a frame rate of, e.g., over 40 or over 50 frames/s. The SLO device receives the SLO beam reflected from the retina at step 210. In the SLO device, the reflected light goes through a confocal filter that transmits light from the retina and blocks the other reflected light. A display displays images (e.g., a video) at step 212 that show the floater shadow on the retina.

The floater shadow is tracked at step 214 using the SLO image to determine the xy-location of the shadow, as described in more detail with reference to FIG. 6. The angular scanning range may be changed at step 216. The image may show a region with the floater shadow, and a smaller angular range (e.g., be 2 to 10 degrees, such as approximately 5 degrees) may be used to narrow the angular scanning to that region. Since the angular scanning range is smaller, a higher frame rate may be used, e.g., over 100 frames/s. If the angular scanning is to be changed at step 216, the method returns to steps 210 and 214 to scan the different angular range and display the resulting image. If the angular scanning range is not to be changed at step 216, the method proceeds to step 218 to determine whether the floater is clinically significant.

The floater may be clinically significant, i.e., may be expected to cause a visual disturbance, at step 218. The floater shadow may be evaluated to determine the clinical significance of the floater, as described in more detail with reference to FIGS. 2 and 8. If the floater is not clinically significant at step 218, the method proceeds to step 220 to check the next floater shadow. If the floater is clinically significant at step 218, the method proceeds to step 224.

The interferometer device determines the z-location and sends the z-location to the laser device at step 224, so that the laser device can aim the focal point of the laser beam at the z-location, as described in more detail with reference to FIG. 6. The interferometer device may aim the interferometer beam at the xy-location of the floater shadow tracked by a tracking computer program to perform an A-scan in this direction. For example, a SSASI device may perform an A-scan in this direction, or an OCT device may perform A-scans in a small angular range (e.g., +/− two degrees) centered in this direction. The interferometer device may perform any suitable number of scans, e.g., a value in a range of 1 to 100, or 5 to 50, or 10 to 20 scans. In certain embodiments, the computer determines whether the expected radiance energy at the retina from a laser beam aimed at the z-location is safe, as described in more detail with reference to FIG. 1.

Via steps 212 and 224, the surgical system determines the xy-location of the floater shadow and z-location of the floater, as described in more detail with reference to FIG. 6. In certain embodiments, the xy-location is the location predicted for when the laser fires. The laser device directs the laser beam through the xy-scanner to the z-location of the floater at step 226. The xy-scanner directs the laser beam to the xy-location determined by the tracking at step 222. The method then proceeds to step 220 to check whether there is a next floater shadow. If there is a next floater shadow, the method returns to step 210, where the SLO device sends the SLO beam through the xy-scanner towards the next floater shadow. If there is no next floater shadow, the method ends.

In certain embodiments, laser device 22 is optimized prior to treatment. In the embodiments, the laser beam is directed near the floater using subthreshold energy levels. A feedback signal (e.g., a two-photon fluorescence or a second harmonic feedback signal) from the vitreous is detected. Adaptive optics (e.g., an adaptive mirror) in the laser beam path are used to maximize the intensity of the feedback signal to minimize aberrations of the eye and the optical system.

Figure 8:
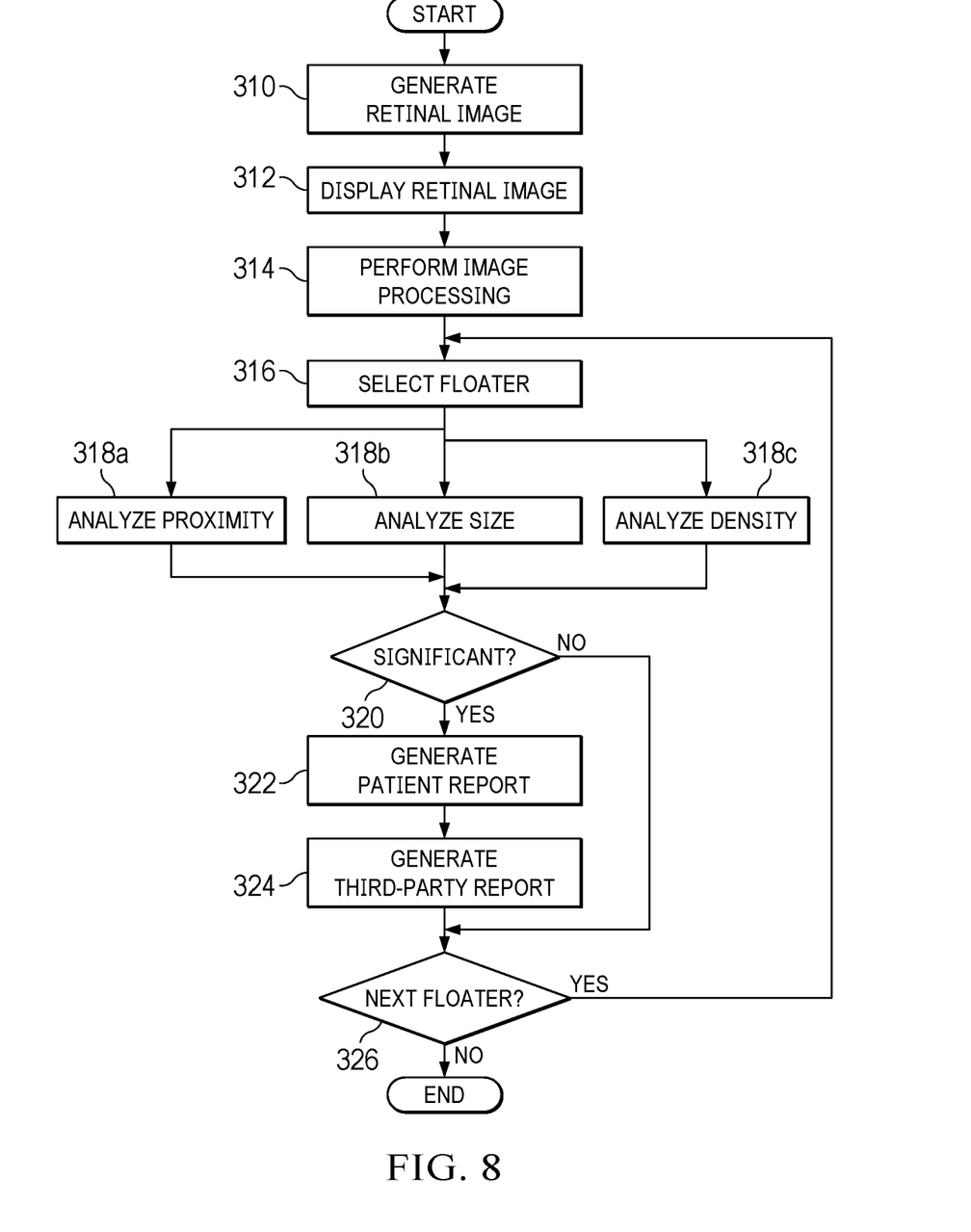
FIG. 8 illustrates an example of a method for evaluating floaters, which may be performed by the system of FIG. 1, according to certain embodiments.

FIG. 8 illustrates an example of a method for evaluating floaters, which may be performed by system 10 of FIG. 1, according to certain embodiments. In the example, the method generates a retinal image of an eye and analyzes floater shadows of the image to evaluate floaters in the eye. The method starts at step 310, where an SLO device generates a retinal image of an eye. A computer displays the image on a display at step 312. The computer performs image processing on the image at step 314. An image processing program may detect the edges of a floater shadow indicating the presence of a floater. In certain embodiments, the computer overlays a graphical element onto the image that point out the shadow to a user, e.g., a circle that surrounds the shadow, an arrow that points to the shadow, or a border that outlines the shadow.

A shadow is selected to be analyzed at step 316. The user or the computer may select the shadow. Steps 318*a*, 318*b*, and 318*c* describe analyzing the shadow to determine if the floater is clinically significant, as described in more detail with respect to FIG. 2. The proximity of the shadow to the fovea or parafovea is analyzed at step 318*a*. For example, a shadow on or passing over the fovea or parafovea may indicate a clinically significant floater. The size of the shadow is analyzed at step 318*b*. For example, a shadow larger than a critical size may indicate a clinically significant floater. The density of the shadow is analyzed at step 318*b*. For example, a shadow with a higher contrast relative to the background may indicate a clinically significant floater.

The method may include steps 318*a*, 318*b*, and/or 318*c*, i.e., the method need not include all the steps. In addition, the user and/or computer performs any or all of the included steps. In some cases, the user may decide to perform one or more steps, and then instruct the computer to perform other steps. Also, if the outcome of one step indicates that a floater is significant, the method may omit the remaining steps. For example, if steps 318*a* and 318*b* indicate the floater shadow is in the foveal region and is critically large, the method may omit step 318*c*. Alternatively, if the outcome of one step indicates that a floater is not significant, the method may omit the remaining steps. For example, if step 318*a* indicates the floater shadow is far from the parafoveal region, the method may omit steps 318*b* and 318*c*.

The floater may be designated as clinically significant at step 320 in response to the analyses performed at steps 318*a*, 318*b*, and/or 318*c*. The user and/or computer may make this decision. If the floater is significant, the method proceeds to steps 322 and/or 324, where reports are generated, as described in more detail with reference to FIG. 1. The computer generates a patient report at step 322. For example, the patient report can be used to educate the patient about their condition. The computer generates an authorization report at step 324. For example, the authorization report can be used to obtain approval for treatment. In other embodiments of the method, the laser device may treat the floater, as described in more detail with respect to FIGS. 6 and 7, in addition to or as an alternative to generating reports. If the floater is not significant, the method proceeds directly to step 326.

There may be a next shadow in the image at step 326. If there is a next shadow, the method returns to step 316 to select the next shadow. If there are no more shadows, the method ends.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112 (f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic laser surgical system for treating a floater in an eye, comprising:
    a scanning laser ophthalmoscope (SLO) device configured to:
        generate an SLO image of a floater shadow cast by the floater onto a retina of the eye; and
        provide an xy-location of the floater shadow, the xy-location related to an xy-scanner;
    an interferometer device configured to provide a z-location of the floater, the z-location relative to the retina;
    a laser device configured to generate a laser beam, the laser device comprising a z-focusing component configured to:
        focus a focal point of the laser beam onto the z-location of the floater; and
    the xy-scanner configured to:
        receive an SLO beam from the SLO device and direct the SLO beam along an SLO beam path towards the xy-location of the floater shadow; and
        receive the laser beam from the laser device and direct the laser beam along the SLO beam path towards the xy-location of the floater shadow.

2. The ophthalmic laser surgical system of claim 1, the interferometer device comprising an optical coherence tomography (OCT) device.

3. The ophthalmic laser surgical system of claim 1, the interferometer device comprising a swept source A-scan interferometer (SSASI) device.

4. The ophthalmic laser surgical system of claim 1, the interferometer device comprising a plurality of reference arms, each arm corresponding to a z-range of a plurality of z-ranges within a vitreous of the eye, a z-range relative to the retina.

5. The ophthalmic laser surgical system of claim 1, further comprising an xy-encoder configured to:
    detect an angular position of the xy-scanner, the angular position corresponding to an xy-location expressed in encoder units; and
    report the xy-location expressed in encoder units.

6. The ophthalmic laser surgical system of claim 5, the laser device comprising:
    adaptive optics configured to minimize a spot size of the laser beam.

7. The ophthalmic laser surgical system of claim 5, the laser device comprising:
    adaptive optics configured to maximize a feedback signal to optimize the laser beam.

8. The ophthalmic laser surgical system of claim 5, the laser device comprising:
    an optical element configured to form the laser beam as a Bessel or Bessel-like long focal length beam.

9. The ophthalmic laser surgical system of claim 1, further comprising a computer, the computer configured to:
    perform image processing on the SLO image of the floater shadow cast onto the retina;
    evaluate the floater shadow to determine if the floater can cause a visual disturbance; and
    output results of the evaluation.

10. The ophthalmic laser surgical system of claim 9, the computer configured to evaluate the floater shadow to determine if the floater can cause a visual disturbance by:
    determining if the floater shadow is cast onto a foveal region or a parafoveal region of the eye.

11. The ophthalmic laser surgical system of claim 9, the computer configured to evaluate the floater shadow to determine if the floater can cause a visual disturbance by:
    determining if the floater shadow is larger than a critical shadow size.

12. The ophthalmic laser surgical system of claim 9, the computer further configured to:
    generate a report comprising:
        the SLO image of the floater shadow cast onto the retina; and
        educational information about the floater or a recommended treatment for the floater, and output the report.

13. A method for treating a floater in an eye, comprising:
generating, by a scanning laser ophthalmoscope (SLO) device, an SLO image of a floater shadow cast by the floater onto a retina of the eye;
providing, by the SLO device, an xy-location of the floater shadow, the xy-location related to an xy-scanner;
providing, by an interferometer device, a z-location of the floater, the z-location relative to the retina;
generating, by a laser device, a laser beam;
focusing, by a z-focusing component of the laser device, a focal point of the laser beam onto the z-location of the floater;
receiving, by the xy-scanner, an SLO beam from the SLO device and directing the SLO beam along an SLO beam path towards the xy-location of the floater shadow; and
receiving, by the xy-scanner, the laser beam from the laser device and directing the laser beam along the SLO beam path towards the xy-location of the floater shadow.

14. The method of claim 13, the interferometer device comprising an optical coherence tomography (OCT) device.

15. The method of claim 13, the interferometer device comprising a swept source A-scan interferometer (SSASI) device.

16. The method of claim 13, further comprising:
detecting, by an xy-encoder, an angular position of the xy-scanner, the angular position corresponding to an xy-location expressed in encoder units; and
reporting, by the xy-encoder, the xy-location expressed in encoder units.

17. The method of claim 13, further comprising:
performing, by a computer, image processing on the SLO image of the floater shadow cast onto the retina;
evaluating, by the computer, the floater shadow to determine if the floater can cause a visual disturbance; and
outputting results of the evaluation.

18. The method of claim 17, the evaluating the floater shadow to determine if the floater can cause a visual disturbance comprising:
determining if the floater shadow is cast onto a foveal region or a parafoveal region of the eye.

19. The method of claim 17, the evaluating the floater shadow to determine if the floater can cause a visual disturbance comprising:
determining if the floater shadow is larger than a critical shadow size.

20. The method of claim 17, further comprising:
generating, by the computer, a report comprising:
the SLO image of the floater shadow cast onto the retina; and
educational information about the floater or a recommended treatment for the floater; and
output the report.

* * * * *